(12) United States Patent
Kumar et al.

(10) Patent No.: US 8,080,403 B2
(45) Date of Patent: Dec. 20, 2011

(54) BIOLOGICAL PROCESS FOR COLOR REDUCTION OF PULP AND PAPER EFFLUENT

(75) Inventors: Rita Kumar, New Delhi (IN); Anil Kumar, New Delhi (IN); Deepa Kachroo Tiku, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 391 days.

(21) Appl. No.: 12/320,370

(22) Filed: Jan. 23, 2009

(65) Prior Publication Data

US 2009/0191612 A1    Jul. 30, 2009

Related U.S. Application Data

(60) Continuation-in-part of application No. 11/077,217, filed on Mar. 11, 2005, now abandoned, which is a division of application No. 10/393,354, filed on Mar. 21, 2003, now Pat. No. 6,896,806.

(60) Provisional application No. 60/365,808, filed on Mar. 21, 2002.

(51) Int. Cl.
*C12N 1/20* (2006.01)

(52) U.S. Cl. .................... 435/253.3; 435/262.5

(58) Field of Classification Search .............. None
See application file for complete search history.

(56) References Cited

U.S. PATENT DOCUMENTS 4,266,035 A * 5/1981 Blair et al. ................ 435/253.3
4,444,888 A    4/1984 Blair et al.

FOREIGN PATENT DOCUMENTS

JP    2002-028691 A    1/2002

OTHER PUBLICATIONS

Clausen, Carol A., "Bacterial Associations with Decaying Wood: a Review", International Biodeterioration & Biodegradation, 1996, pp. 101-107.

* cited by examiner

*Primary Examiner* — Irene Marx
(74) *Attorney, Agent, or Firm* — Foley & Lardner LLP

(57) ABSTRACT

The present invention relates to a bacterium strain of accession no. MTCC 5099, a process for the preparation of inoculum of the said strain, and a process for the reduction of color from pulp mill effluent using the above said inoculum, which comprises steps of inoculating appropriate aliquots of the pulp and paper mill effluent with the cell slurry obtained, incubating the mixture at about 37 degree C. at about 100 rpm for time duration ranging between 24-48 hours, assessing color and total lignin levels to determine the color removal efficiency of the above said bacterium.

5 Claims, 1 Drawing Sheet

BIOLOGICAL PROCESS FOR COLOR REDUCTION OF PULP AND PAPER EFFLUENT

Figure 1A:
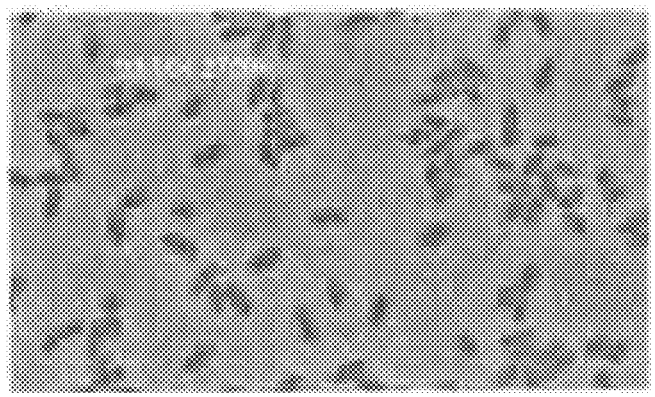

This application is a continuation-in-part of U.S. patent application Ser. No. 11/077,217, filed Mar. 11, 2005, which is a divisional application of U.S. patent application Ser. No. 10/393,354, filed Mar. 21, 2003, which issued as U.S. Pat. No. 6,896,806 on May 24, 2005, and claims the benefit of U.S. Provisional Patent Application No. 60/365,808, filed Mar. 21, 2002, the respective contents of which are incorporated fully herein by reference.

FIELD OF THE PRESENT INVENTION

The present invention relates to a bacterium strain of accession no. MTCC 5099, a process for the preparation of inoculum of the said strain, and a process for the reduction of color from pulp mill effluent using the above said inoculum, which comprises steps of inoculating appropriate aliquots of the pulp and paper mill effluent with the cell slurry obtained, incubating the mixture at about 37° C. at about 100 rpm for time duration ranging between 24-48 hours, assessing color and total lignin levels to determine the color removal efficiency of the above said bacterium.

BACKGROUND AND PRIOR ART REFERENCES OF THE PRESENT INVENTION

The problem of color removal from pulp and paper mill waste has been a subject of great consideration and investigation in the last few decades. An estimated two trillion gallons of wastewaters are discharged annually by the pulp and paper industry in major paper-producing countries and much of this effluent is highly colored. (Joyce et al., 1983).

The brownish color of the wastewater is mainly organic in nature primarily attributable to lignin degradation products formed during various pulping and bleaching operations (Srivastava et al., 1984, Dilek et al., 2000). The other color-imparting agents are wood-extractives, tannins, resins and synthetic dyes.

Color was never thought to be a major problem, being classified as a non-conventional pollutant. Some reasons for regulating color of waste water to protect fisheries or for aesthetic reasons. Additionally, the discharge of colored pulping effluents to the receiving waters has shown to inhibit photosynthetic activity of aquatic biota by reducing the penetration of sunlight and also have a direct toxic effects on biota.

The color compounds also chelate metal ions and may impart contamination due to heavy metals. Color causing organic compounds have also been implicated in the appearance of blue-green algal blooms (Paerl, 1982; Kuenzler et al., 1982; Witherspoon & Pierce, 1982). It is therefore, imperative that the color present in pulp and paper mill effluents be removed, before being discharged into receiving waters.

There are two general strategies for the removal of color from the effluent of a pulp & paper mill:
1) Conventional end of pipe treatment
2) Modification of the pulp and paper manufacturing process so that less color is produced.

The following technologies are conventionally used for removing color:
Secondary treatment in which the effluents are treated with conventional activated sludge method. However, conventional biological treatment systems cannot remove color (Yosefian et al., 2000).
Enzyme pre-treatment
Resin separation and ion exchange
Aluminum oxide
Adsorption on wood
Membrane processes
Irradiation
Electrolytic process
Activated carbon
Land treatment
Ozone At this point, no single technology has been identified as being the most effective for color removal. Since all the above-cited technologies are cost-intensive, they would have adverse economic impact on the mill involved. Moreover, chemical treatment processes add up to the ever-increasing concentration of chemicals in the environment (Kapdam et al., 2000).

In principle, decolorization is achievable using one or a combination of the following methods;
Adsorption
Filtration
Precipitation
Chemical degradation
Photodegradation and
Biodegradation Rohella et al., 2001 used polyelectrolytes (commercially available) for removing color from pulp mill effluents. However, it remains to be seen if this method for removing color is cost effective. Because polyelectrolytes rely on ionic charge of the effluent, the color reducing ability of a method employing polyelectrolytes will be highly variable, considering the enormous fluctuations occurring in the composition of the wastewater.

The majority of color removal techniques work either by concentrating the color into a sludge or by the partial breakdown or complete breakdown of the colored molecule (Willmott et al, 1998). However, the color and chemical composition of the pulp mill effluents are usually subject to both daily process as well as seasonal variations. A single, universally applicable end-of-pipe solution has therefore not emerged to date. General physico-chemical color removal methods such as chemical precipitation, rapid sand filtration, membrane processes and adsorption have been developed (Springer, 1985). Adsorption and membrane processes, although efficient are expensive (Manjunath and Mehrotra, 1981).

Application of electrochemical methods is another way to treat wastewaters generated from cellulose paper production plants (Christoskova and Lazarov, 1988). This method guarantees high treatment efficiency but its effectiveness depends upon the types of electrodes, the construction of electrocoagulators and the conditions under which the process is run.

Chemical precipitation, using alum, ferric chloride and lime has also been studied extensively (Lathia and Joyce, 1978; Dugal et al, 1976; Joyce et al, 1979; Srivastava et al, 1984; Beulker and Jekel, 1993; Stephenson & Duff, 1996). In spite of short retention times and low capital costs, there are some drawbacks, such as the high cost of chemicals for precipitation as well as for adjusting pH, the formation of voluminous sludge due to heavy dosages of the chemicals used, problems associated with dewatering and disposing of the generated sludge as well as the high residual cation levels in the sludge, so that their color remains in the supernatant (Stephenson and Duff, 1996; Srivastava et al, 1984).

In theory, biological treatment provides an ideal solution for removing color from the effluents of pulp and paper mills. Biological treatment of the effluent produces less sludge as compared to sludge produced when a chemical treatment process is employed. Lower daily running costs are also incurred. Among the biological systems, white-rot fungi have been extensively researched upon, for their capability to degrade lignin which forms an important and major component of the pulp and paper effluents (Feijoo et al., 1995). Certain workers have shown that the pellets of white-rot fungi, under specific conditions of incubation, strongly adsorb color and AOX from the kraft bleach plant effluent (Jaspers et al., 1996).

Raghu Kumar et al., 1996, showed that marine fungi could also be utilized for removing color from bleached plant effluent. One of the strain was reported to give 74% decolorization at alkaline pH over a period of 14 days. Several other researchers have also reported partial decolorization by white-rot fungi (Eaton et al, 1980; Livernoche et al, 1983; Pronty, 1990; Gokcay and Dilek, 1994). Gokcay and Dilek (1994) have pointed out that due to the need for high glucose concentrations by the fungus, this treatment is economically non-feasible. They have also reported that the fungi were not as effective when bleaching effluents are present.

Dilek et al., 1999 have reported the decolorization of pulping effluents using a mixed culture algae. A combination of aerobic-anaerobic treatment has been used by Vidal et al. White-rot fungi excreting several extracellular oxidative enzymes including Lignin peroxidase, Manganese peroxidase and laccases were used for decolorizing bleach kraft pulp mill effluents. Up to 64% color was removed by applying aerobic-anaerobic treatment followed by enzyme treatment.

To date, there are almost no reports regarding the utilization of pure bacterial cultures for decolorization of pulping effluent. The novelty of the present invention is the application of pure cultures of bacteria, isolated from natural habitat, for removing color of the pulp and paper wastewaters in an industrially and economically viable fashion.

FIGURES

Figure 1B:
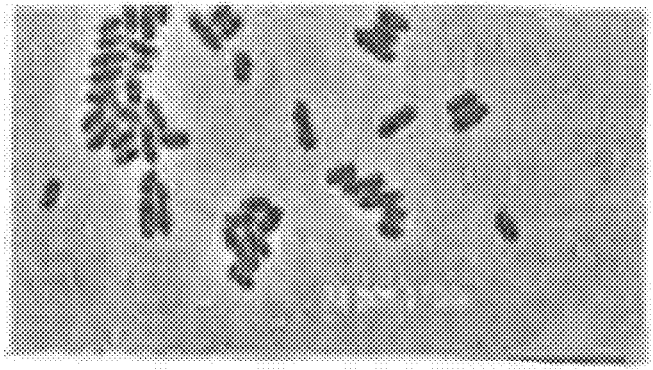

FIGS. 1A and 1B are pictures of a sample of bacterial strains 7 and 8 when viewed under high magnification.

OBJECTS OF THE PRESENT INVENTION

The main object of the present invention is to provide a process for the aerobic treatment of pulp mill wastewater for color reduction.

Another object of the present invention is to provide a bacterial strain for color reduction of paper and pulp effluent.

Still another object of the present invention is to develop an inoculum of the strain for color reduction of paper and pulp effluents.

SUMMARY OF THE PRESENT INVENTION

The present invention relates to a biologically pure culture of bacterial strain *Pseudomonas aeruginosa* (DSMZ 03-505) having accession no. MTCC 5099. The claimed strain of *Pseudomonas aeruginosa* are gram negative short rods. The inventive strain of bacteria decolorize wastewater by about 70% within a period of 24 hours and are viable in the waste water effluent after decolorization.

DETAILED DESCRIPTION OF THE PRESENT INVENTION

The present invention relates to a bacterium strain of accession no. MTCC 5099, a process for the preparation of inoculum of the strain, and a process for the reduction of color from pulp mill effluent using the above said inoculum, which comprises steps of inoculating appropriate aliquots of the pulp and paper mill effluent with the bacterial inoculum, for color reduction studies along with a control flask containing effluent sample without any added inoculum. The flasks are then incubated at 37° C./rpm for 48 hours. Samples are withdrawn from the flasks in 50 ml aliquots and processed for assessing color and total lignin levels. This permits an analysis of the color removal efficiency of the claimed bacterium strain.

In another embodiment of the present invention, the bacterium strain is identified as having Accession No. MTCC 5099. Morphological and biochemical studies indicate the bacteria to be short gram negative rods identified as *Pseudomonas aeruginosa* (DSMZ 03-505).

In still another embodiment of the present invention, wherein a process for the preparation of inoculum of the strain of claim 1, said process comprises of:

i) isolating a bacterium from activated sludge collected from the effluent treatment plant of a pulp and paper mill, ii) culturing the said bacterium on nutrient agar media containing 0.1% w/v each of lignin, tannin and vanillin to get pure cultures, iii) inoculating the said bacterium in nutrient broth containing 0.01% Tween 80 to obtain starter culture, iv) culturing the above bacterium for obtaining required biomass by inoculating the appropriate aliquot of nutrient broth, with the starter culture and incubating the above medium at 37° C./100 rpm for 16-18 hours, v) centrifuging the resulting culture, after attaining an optical density of 1.5-2.0, to obtain pellet, washing the collected pellet by dissolving in $PO_4^{-3}$ buffer, 0.05M, pH 6.8, recentrifuging the pellet, and vi) collecting the pellet obtained from step (v), resuspending the pellet in 10 ml of 0.05M $PO_4^{-3}$ buffer, pH 6.8, to obtain cell slurry for decolorization studies.

In still another embodiment of the present invention, wherein the inoculum for using in color reduction experiments is obtained by inoculating the above said bacterium in nutrient broth containing 0.01% Tween 80 to obtain starter culture.

In still another embodiment of the present invention, wherein the above said starter culture is used for obtaining the required inoculum by inoculating appropriate aliquot of nutrient broth, with the starter culture and incubating the above medium at 37° C./100 rpm for 16-18 hours;

In still another embodiment of the present invention, wherein the resultant culture is centrifuged at appropriate rpm, preferably 6000 rpm for a period of 20 minutes at 4° C. The resultant pellet is washed by resuspending in 0.05M $PO_4^{-3}$ buffer, pH 6.8 and recentrifuging the pellet. In still another embodiment of the present invention, wherein the resultant pellet is dissolved in 10 ml of 0.05M $PO_4^{-3}$ buffer, pH 6.8, to obtain inoculum for color reduction studies;

The present invention also provides a method for removing color from pulp mill effluent using the above said inoculum, which comprises:

i) inoculating appropriate aliquots of the pulp and paper mill effluent with a cell slurry of the claimed bacteria strain, for color reduction studies along with a control flask containing effluent sample without any added inoculum;

ii) incubating the flasks set up in step (a) at 37° C./100 rpm for 48 hours;

iii) withdrawing samples from the above flasks in 50 ml aliquots and processing them to assess color and total lignin levels, iv) analyzing the color removal efficiency of the above said bacterium by comparing the color levels of the treated effluent, with the color level of control sample after 24 and 48-hour intervals, v) checking the viability of the bacteria in the effluent by culturing the bacteria in the effluent on nutrient agar medium and calculating CFU/ml.

In still another embodiment of the present invention, wherein the viability of the above said culture is checked by plating dilutions of sample taken from the experiment to obtain separate colonies and calculating CFU/ml of the same after 24 and 48 hour intervals.

In still another embodiment of the present invention, an aerobic, biological decolorization process is described using a bacterial isolate, obtained from activated sludge of a pulp and paper mill ETP, which gives up to 55% reduction in color levels of the given effluent.

In one embodiment of the present invention, the strain shows color reduction of 55% in 24 hrs.

In still another embodiment of the present invention, wherein the strain shows color reduction of 60% in 48 hrs.

In still another embodiment, the strain shows color reduction of 70% in 24 hrs.

In another embodiment, the ratio of effluent to biomass is about 1:1.

In still another embodiment of the present invention, the strain is viable after the color reduction.

The invention also provides a biological process for the reduction of color from pulp and paper mill effluent. Also disclosed is a bacterial strain isolated from a specific source, capable of reducing color from pulp and paper effluent. The said bacterial isolate is able to reduce the color of the effluent.

The present invention also relates to a biological process for color reduction from pulp and paper mill effluent using an aerobic bacterial strain isolated from specific source from the pulp and paper mill.

In still another embodiment of the present invention, the present invention provides a process for the reduction of from a pulp mill effluent using aerobic treatment process. An aerobic bacterial strain was isolated from a specific source of the pulp and paper mill and used for decolorization of the pulp mill effluent.

The bacterial isolate according to the present invention is presently deposited at IGIB as CBTCC/and its identification is underway.

In still another embodiment of the present invention, the bacterial isolate facilitates the reduction of color from pulp and paper effluent.

In still another embodiment of the present invention, the bacterium described in the said invention is isolated from activated sludge of effluent treatment plant of a pulp and paper mill as follows. 5.0 grams of homogenized activated sludge taken from effluent treatment plant of pulp and paper mill is inoculated in the enrichment medium. The enrichment medium consists of 100 ml of sludge infusion, 25 ml of sterile nutrient broth and 0.1% (w/v) each of lignin (Alkali lignin-Aldrich, USA), vanillin and tannin (Sigma). The pH is adjusted to 6.8±0.2.

In still another embodiment of the present invention, wherein the sludge extract is prepared by boiling a mixture containing 300 ml of sludge in 1200 ml of triple distilled water for about 30 minutes. The resultant mixture is cooled, centrifuged and coarse filtered. The final filtrate obtained is autoclaved at 121° C., 15 psi for 20 minutes and used for preparing the enrichment medium. The enrichment medium inoculated with activated sludge is incubated at 37° C. for 24-48 hours to obtain an enriched culture.

In still another embodiment of the present invention, the enriched culture is serially diluted to $10^{-12}$ using 0.05M $NaH_2PO_4$—$Na_2HPO_4$ buffer, pH 7.0. Stock solutions of lignin, vanillin and tannin are prepared. Nutrient broth containing 2% agar is prepared and 0.2% (v/v) each of lignin, vanillin and tannin are added from their stock solutions. The serially diluted inoculum is then plated and incubated at 37° C. for 24-48 hours. A single isolated colony is picked and streaked on a fresh plate in the same medium. The above step is repeated twice, till pure colonies are obtained.

In still another embodiment of the present invention, the above mentioned bacterium is inoculated with the help of sterile nichrome loop into 15-20 ml sterile nutrient broth (NB) containing (per liter), 5.0 g peptic digest of animal tissue, 5.0 g of sodium chloride, 1.5 g of beef extract, 1.5 g of yeast extract and 0.2 ml Tween-80. The culture is incubated at 37° C. for approximately 16-18 hours in an incubator shaker. For gentle shaking, the incubator shaker is maintained at an appropriate rpm, preferably 100 rpm. After sufficient growth is obtained, the broth was stored at 4° C. till further use. 250 ml of sterile NB is inoculated with 250 µl of the above prepared starter culture.

In still another embodiment of the present invention, the flask is kept for incubation at 37° C./100 rpm for 16-18 hours till an optical density (650 nm) of 1.5-2.0 is achieved. The cells are harvested by centrifuging at an appropriate rpm, preferably 6000 rpm for 20 minutes. The resultant pellet is washed by resuspending it in a minimum quantity of 0.05M phosphate buffer, pH 6.8 followed by centrifugation at the same rpm and for the same time mentioned above. During centrifugation, the temperature is maintained at 4° C. The pellet thus obtained, is resuspended in minimum volume of 0.05M phosphate buffer, pH 6.8, preferably 10 ml and vortexed to make a homogeneous suspension that is used for reducing color from the pulp and paper effluent.

In still another embodiment of the present invention, wherein For setting up the color reduction experiments, 250 ml of sample is taken in screw-capped conical shake flasks. The inoculum is added to the effluent sample after checking the pH of the effluent to be preferably around 7.0. Control flask which does not contain any added inoculum is also maintained for comparison. The flasks are incubated at 37° C./100 rpm for a period of 48 hours.

In still another embodiment of the present invention, analysis of the extent of the color reducing efficiency using the inventive bacterial strain is carried out in addition to determining the total lignin levels. Analysis is performed by withdrawing approximately 50 ml of samples, centrifuging them at appropriate rpm, preferably 8000 rpm for 30 minutes at 4° C. and passing the resultant supernatant through 0.451µ filters (Millipore). For measuring the color levels, pH of the samples is adjusted to 7.6 and the optical density of the sample is measured at 465 nm as described in NCASI color estimation method. The total lignin assay is also carried out by the Modified Pearl Benson method.

Another embodiment of the present invention, allows assessing the viability of the culture during the entire experiment. Here a sample is diluted serially and plated on nutrient agar medium and incubated at 37° C., overnight in an inverted position. The colonies were counted and colony forming units/ml (CFU/ml) calculated.

The present invention also provides a process for the preparation of an inoculum of the said bacterium and using it for reduction of color from pulp and paper industrial effluent. The inventive process comprises:

a) isolating a bacterium from activated sludge collected from the effluent treatment plant of a pulp and paper mill;

b) culturing the said bacterium on nutrient agar media containing 0.1% w/v each of lignin, tannin and vanillin to get pure cultures;

c) inoculating the said bacterium in nutrient broth containing 0.01% Tween 80 to obtain starter culture;

d) culturing the above bacterium for obtaining required biomass by inoculating appropriate aliquot of nutrient broth, with the starter culture and incubating the above medium at 37° C./100 rpm for 16-18 hours;

e) centrifuging the resulting culture, after attaining an optical density of 1.5-2.0, to obtain pellet, washing the collected pellet by dissolving in 0.05M, $PO_4^{-3}$ buffer, pH 6.8 and recentrifuging to pellet;

f) collecting the pellet obtained from step (e), dissolving in 10 ml of 0.05M, $PO_4$-3 buffer, pH 6.8, to obtain cell slurry for color reduction studies;

g) inoculating appropriate aliquots of the pulp and paper mill effluent with the cell slurry obtained in step (f) for color reduction studies along with a control flask containing effluent sample without any added inoculum;

h) incubating the flasks set up in step (g) at 37° C./100 rpm for 48 hours;

i) withdrawing samples from the above flasks in 50 ml aliquots and processing them for assessing color and total lignin levels;

j) analyzing the color removal efficiency of the above said bacterium by comparing with the color level of control sample after 24 and 48-hour intervals;

k) checking the viability of the above bacterium in the effluent by colony counting method and calculating the CFU/ml after 24 and 48-hours.

In an embodiment of the present invention, the bacterium is isolated from activated sludge collected from the effluent treatment plant of a pulp and paper mill.

In accordance with one embodiment of the present invention, the above mentioned bacterium is inoculated in nutrient broth containing 0.01% Tween 80 to obtain the starter culture.

In another embodiment, a culture of the bacterium is prepared by inoculating nutrient broth with starter culture.

In still another embodiment, the incubation of the bacterial strains is carried out by gentle agitation at 100 rpm.

In yet another aspect, the growth of the incubated bacterial strains is carried out at a temperature of 37° C. for a period of 16-18 hours.

Following incubation to achieve an optical density of approximately 1.5-2.0, the bacterial culture is centrifuged at appropriate rpm preferably 6000 rpm for a period of approximately 20 minutes at 4° C.

In a further embodiment of the present invention, the resultant pellet is washed by resuspending it in minimum quantity of phosphate buffer, 0.05 M, pH 6.8 and recentrifuged using the same rpm and time conditions. During centrifugation, the temperature is maintained at 4° C.

In a further embodiment of the present invention. The pellet thus obtained, is resuspended in minimum volume of phosphate buffer, 0.05M, pH 6.8, preferably 10 ml and vortexed to make a homogeneous suspension.

In one of the embodiment of the present invention, the cell slurry obtained above is used for inoculating the effluent samples for reducing color.

The invention further provides a method for the reduction of color levels from a pulp and paper mill effluent.

In another embodiment of the present invention, the flasks containing the above inoculum are incubated at 37° C. at 120 rpm for 48 hours.

In a further embodiment of the present invention, the reduction in color and total lignin levels are observed over a period of 48 hours.

In another embodiment of the present invention, the culture is grown on plates containing nutrient agar medium for viability of the bacterium in the said effluent.

As described in U.S. Provisional Patent No. 60/365,808, filed Mar. 21, 2002, which is incorporated herein in its entirety, it is found that bacterial consortia are able to reduce color of the effluent over a period of five days. However, studies have been performed to reduce the retention time (make the process faster) and enhance the extent of color reduction in the effluent. Approximately 58% reduction in the color levels within a period of 24 hours by a single bacterial isolate is observed as compared to a 51% reduction in color over a 3-5 day period when a bacterial consortia is used. Therefore, in the complete patent specification, the results obtained by using the individual bacterial isolate have been presented; being markedly better than those obtained by the bacterial consortia.

2. The culture has been already sent for deposit to IMTECH in the international depository and number shall be allotted by 17 Mar. 2003.

3. We would like to claim for only the one bacterial isolate which has repeatedly given best results as given in table 5 and 8 of complete specification.

The strain of the instant Application is deposited in MTCC, Chandigarh INDIA and has been assigned an Accession No. MTCC 5099. The strain is mentioned as bacterial strain Bacterium B4 in the specification at several places.

The invention of the instant Application is further elaborated in the form of examples. However, these examples merely substantiate the invention and do not construe to limit the scope of the invention.

EXAMPLE I

Bacteria are isolated from wastewater emerging from both inlet as well as outlet of Effluent Treatment Plant. The pH of the effluent is checked and found to be 7.6±0.2. Filtered and autoclaved wastewater was used as media for isolating autochthonous bacteria in different percentages viz., 100%, 80%, 50%, 30% and 10% using mineral salts medium (MSM). The composition of the MSM used was as follows:

| | |
|---|---|
| $K_2HPO_4$ | 5 mM |
| $KH_2PO_4$ | 5 mM |
| $MgSO_4 \cdot 7H_2O$ | 1 mM |
| EDTA | 0.3 mM |
| $ZnSO_4 \cdot 7H_2O$ | 0.01 mM |
| $MnSO_4 \cdot 7H_2O$ | 0.02 mM |
| $CuSO_4 \cdot 7H_2O$ | 0.004 mM |
| $FeSO_4 \cdot 7H_2O$ | 0.1 mM |
| $NaMo_4 \cdot 2H_2 0$ | 0.004 mM |
| $(NH_4)_2SO_4 \cdot 7H_2O$ | 5 mM |
| pH | 7.0 .±. 0.2 |

To 100 ml aliquots of Nutrient Broth (NB), 1 ml of the waste water effluent from the inlet and outlet of the effluent treatment plant is added and kept at 37° C./24-48 hrs for enrichment.

Effluent-MSM plates are prepared using 2% agar as solidifying agent. The plates were kept for solidification and inverted till further use. Serial dilution plating is carried out by serially diluting the enriched inoculum till a dilution of 10-12. Serial dilution is carried out by taking 9 ml aliquots of $Na_2HPO_4$—$NaH_2PO_4$ buffer (pH 6.8, 0.05 M) and inoculating 1 ml of enriched inoculum in the first vial, vortexing and taking 1 ml from this vial for further dilutions, until a $10^{-12}$ dilution is obtained. These vials are then used for plating on to the effluent MSM plates.

100 µl of the above dilutions are placed on the different Effluent-MSM plated and spread plated with the help of a sterile glass spreader. All plates are prepared in duplicates and incubated for 24-48 hours at 37° C. Colonies appearing on these plates are marked according to morphological differences and selected for further purification.

Colonies exhibiting different morphological appearance are picked with sterile inoculating needle and streaked on plates containing the respective growth media. After two to three repetitive subculturing, purified isolates are obtained which are tested for purity and stored as slants and stabs in their respective media.

Loopful of cultures are taken and inoculated in sterile aliquots of Nutrient Broth, vortexed and kept for incubation at 37° C./120 rpm for 16-18 hrs. The optical density of the mother cultures is measured at 650 nm.

Thirty-five morphologically different bacteria are screened for their ability to reduce color from pulp mill wastewater. 100 ml sterile NB is inoculated with 100 µl of respective mother cultures and incubated at 37° C./120 rpm for 16-18 hours. The initial and final optical densities at 650 nm were noted. Cultures are harvested at an $OD_{650}$ of 1.5-2.0 by centrifuging at 6000 rpm for 20 minutes at 4° C. The pellet obtained is washed twice using sterile phosphate buffer (pH 6.8, 0.05 M) and resuspended in small volume of the same buffer. This suspension is then used for treatability assay in a ratio of bacteria:effluent of 1:1, i.e., 100 ml of effluent sample is treated with pellet obtained from 100 ml of culture media.

The color removal experiment is carried out in batch culture in conical shake flasks at 37° C. at 120 rpm for a period of five days. Color intensities are measured at 450 nm using NCASI optical density method on zero day, third day and fifth days. Thirteen bacteria gave a reduction of 50% and more on the fifth day (Table 1).

EXAMPLE II

The thirteen individual bacteria exhibiting more than 50% color reduction are selected and nine different bacterial consortia were formulated using random combinations. Individual cultures constituting the formulated consortia were independently grown in nutrient broth by inoculating 100 µl of actively growing cultures in each flask. Cultures are incubated at 37° C./16-18 hrs at 120 rpm until an optical density of 1.5-2.0 was achieved. The cultures were then pooled together according to the consortial composition. Optical density at 650 nm of the pooled culture was measured. The cells of the resulting consortia were harvested by centrifuging at 6000 rpm for 20 minutes at 4° C. and was washed twice with $Na_2HPO_4$—$NaH_2PO_4$ buffer (pH 6.8, 0.05 M). The pellets were then resuspended in 10 ml of phosphate buffer and used for color reduction experiments.

Effluent samples, neutralized to pH 7.0+0.2, are taken in 500 ml aliquots in shake flasks and inoculated with the above prepared pellets in a ratio of 1:1. All the flasks were incubated at 37° C./120 rpm for 3 days. Controls are also maintained, which did not contain any added inoculum, apart from the indigenous flora.

Samples are analyzed for color levels using the NCASI spectrophotometric assay and percentage reduction in color is calculated. Only two consortia exhibited a color reduction of more than 50% (Table 2).

EXAMPLE III

Optimum inoculum size for reducing the color levels is checked by inoculating the consortia in three different ratio, viz., 1:1, 1:0.5, and 1:0.75 (effluent:culture). 100 ml effluent samples are taken in shake flasks and inoculated with the formulated consortia prepared from 100 ml, 50 ml and 75 ml NB aliquots. Experimental conditions, such as the temperature of incubation, time and rpm at which the flasks are shaken is similar to that described in example 2. Color levels measured after treatment for three days. The consortia exhibited the highest color reduction with 1:1 effluent:biomass ratio (Table 3).

EXAMPLE IV

To improve the color removal efficiency, fresh bacteria are isolated from the activated sludge obtained from ETP of a Pulp and Paper Mill. 5.0 grams of homogenized activated sludge taken from ETP of pulp and paper mill is enriched in medium consisting of 100 ml of sludge infusion, 25 ml of sterile nutrient broth and 0.1% (w/v) each of lignin (Alkali lignin-Aldrich, USA), vanillin and tannin (Sigma). The pH is adjusted to 6.8+0.2. Individual bacteria are screened for their capacity to decolorize the paper mill effluent.

Treatability assay is conducted in 100 ml aliquots and individual bacterial pellets screened for their color removal efficiencies. Isolate number 4 is observed to be the best, giving a 68% reduction in color after 48 hours, followed by isolate numbers, 35 (63%) and 19 (60%) respectively (Table 4).

EXAMPLE V

Isolates 4, 19 and 35 are then cultivated individually in two different media—Nutrient Broth (NB) (rich media) and Mineral Salts Medium (minimal medium) with inorganic constituents and glucose (1%) as carbon-source to compare the effect of growth media on the performance of the cultures in removing color for pulp mills wastewaters. The above isolates are also cultured separately for formulating them together in the form of a consortium and tested for the effect of culture media on the efficiency of the consortia to reduce color. Nutrient Broth (NB) is prepared by dissolving (per liter), 5.0 g peptic digest of animal tissue, 5.0 g of sodium chloride, 1.5 g of beef extract, 1.5 g of yeast extract and 0.2 ml Tween-80. Mineral Salts Medium (MSM) is prepared as described in example I. Glucose (1% v/v) taken from its sterile stock solution is also added to MSM to act as a carbon supplement for the bacteria. Color removal assays are conducted in batch cultures in 100 ml aliquots with an incubation temperature of 37° C. and 120 rpm shaking. Samples for color analysis are withdrawn at zero, 24 and 48 hours intervals and analyzed for color levels. Both NB as well as MSM grown cultures exhibited almost similar results (Table 5).

EXAMPLE VI

Isolates 4, 19 and 35, which exhibited more than 60% reduction in color of the pulp mill effluent, are formulated into a consortium and screened for their color reduction abilities along with other formulated consortia which contained randomly combined cultures. Consortia CC17 is found to exhibit the maximum reduction in color, up to 55% color reduction within 48 hours.

EXAMPLE VII

The consortium CC 17 formulated in Example VI is used for color removal of century inlet effluent in the presence of different concentrations of glucose and sucrose, (namely, 0.5, 0.75, 1.0% w/v). 1% glucose is found to be the best supplement giving up to 75% reduction in color within 48 hours. However, the results for formulations containing different concentrations of glucose are not significantly different from each other (Table 7).

EXAMPLE VIII

Although addition of glucose in the wastewater reduces color to a greater extent, the practical feasibility of using glucose is questionable. Hence the inventors decided to improve color removal by increasing the biomass loading in the effluent. Bacterium No. 4, 19 and 35 were grown individually, as described earlier until a higher OD 650 of 1.5-2.0 is reached, (instead of 1.0). The individual bacterial are used to formulate the consortium MTCC 5099. Consortium MTCC 5099 is cultured individually until the growth flask attains an optical density of 1.5-2.0. The bacterial consortium is tested for enhancements in its color removal efficiency. All the other experimental conditions are kept constant. Bacterium number 4 exhibited up to 55% color reduction within 24 hours (Table 8). The total lignin levels of the above bacteria are also estimated using the Modified Pearl Benson Method. Bacterium number 4 exhibited the best response, showing a higher lignin removing ability to other individual bacterial cultures, as well as the consortium using increased biomass loading. Results were replicated thrice.

EXAMPLE IX

Monitoring of biomass levels and viability of isolate 4 throughout the experiment in terms of Colony Forming Units (CFU/ml) is carried out. It is found that at the zero hour, the CFU/ml level is approximately $10^9$ CFU/ml, and remained as such for 24 hours. In fact, the CFU/ml level showed an increase to $10^{10}$ CFU's/ml showing that the cells are completely viable till the end of the experiment. Samples are streaked on solid nutrient medium to match the morphological characters of the original culture with the culture in the effluent and found to be the same.

TABLE 1

Reduction in Color of Century Pulp and Paper Mill Inlet to ETP

| S. No. | Isolate No. | % Reduction in Color (5th Day) |
|---|---|---|
| 1 | 176 | 51* |
| 2 | 177 | 56* |
| 3 | 178 | 35 |
| 4 | 180 | 52* |
| 5 | 183 | 53* |
| 6 | 185 | 55* |
| 7 | 186 | 57* |
| 8 | 188 | 50* |
| 9 | 190 | 36 |
| 10 | 191 | 38 |
| 11 | 193 | 38 |
| 12 | 195 | 50* |
| 13 | 200 | 49 |
| 14 | 201 | 50* |
| 15 | 202 | 50* |
| 16 | 205 | 40 |
| 17 | 206 | 46 |
| 18 | 207 | 46 |
| 19 | 208 | 46 |
| 20 | 209 | 55* |
| 21 | 210 | 40 |
| 22 | 211 | 38 |
| 23 | 218 | 40 |
| 24 | 222 | 40 |
| 25 | 223 | 40 |
| 26 | 225 | 60* |
| 27 | 236 | 42 |
| 28 | 243 | 22 |
| 29 | 245 | 50* |
| 30 | 248 | 32 |
| 31 | 252 | 40 |
| 32 | 262 | 30 |
| 33 | 270 | 22 |
| 34 | 271 | 21 |
| 35 | 239 | 27 |

*Bacteria showing more than 50% color reduction

Note:
All values are means of three experiments

TABLE 2

% Color Reduction of Century ETP Inlet Effluent by Different Formulated Consortia

| S. No. | Consortium | Color Removal (%) | |
|---|---|---|---|
| | | 0-day | $3^{rd}$-day |
| 1 | L1 | 36 | 57 |
| 2 | L2 | 48 | 51 |
| 3 | C2 | 39 | 63 |
| 4 | C3 | 41 | 60 |
| 5 | C5 | 51* | 58 |
| 6 | C6 | 30 | 63 |
| 7 | C7 | 60* | 60 |
| 8 | C8 | 35 | 57 |
| 9 | C9 | 48 | 58 |
| 10 | Control | Nil | Nil |

*Consortia exhibiting more than 50% on the O day.
All values are a mean of triplicate analyses with an S.D. of ±0.2

TABLE 3

% Color reduction of Century ETP inlet effluent by different formulated consortia

| S. No. | Consortia Number | % Reduction in color after 3 days | | |
|---|---|---|---|---|
| | | 1:1 | 1:0.75 | 1:0.5 |
| 1 | L1 | 56 | 51 | 45 |
| 2 | L2 | 52 | 48 | 39 |
| 3 | C2 | 65 | 53 | 38 |
| 4 | C3 | 61 | 50 | 46 |
| 5 | C5 | 59 | 49 | 40 |
| 6 | C6 | 60 | 51 | 37 |
| 7 | C7 | 60 | 50 | 35 |
| 8 | C8 | 55 | 43 | 29 |
| 9 | C9 | 55 | 44 | 25 |
| 10 | Control | Nil | | Nil |

All values are a mean of triplicate analyses with an S.D. of ±0.2

TABLE 4

% Removal of Color by Different Bacterial Isolates After 48 Hours

| Culture No. | % Reduction in color |
|---|---|
| 4 | 68 |
| 18 | 55 |
| 25 | 58 |
| 32 | 55 |
| 33 | 51 |
| 34 | 51 |
| 35 | 63 |
| 36 | 51 |
| 22 | 48 |
| 20 | 56 |
| 19 | 60 |
| Control | Nil |

All values are a mean of triplicate analyses with an S.D. of .±.0.2

TABLE 5

% Reduction in Color from pulp mill effluent by Individual Isolates and their formulated consortium

| | 24 hrs | | 48 hrs | |
|---|---|---|---|---|
| Isolate No. | NB-grown | MSM-grown | NB-grown | MSM-grown |
| 4 | 58 | 56 | 68 | 67 |
| 19 | 49 | 48 | 61 | 60 |
| 35 | 49 | 46 | 58 | 59 |
| Control | 48 | 46 | 49 | 51 |

All values are a mean of triplicate analyses with an S.D. of .±.0.2

TABLE 6

% Reduction of Color of Pulp Mill Effluent by Different Formulated Consortia

| | | % Reduction in color | | | |
|---|---|---|---|---|---|
| S. No. | Consortia No. | 24 hrs | 48 hrs | 72 hrs | 96 hrs |
| 1 | CC1 | 17 | 22 | 53 | 53 |
| 2 | CC2 | 11 | 24 | 39 | 41 |
| 3 | CC3 | 11 | 26 | 48 | 50 |
| 4 | CC4 | 11 | 29 | 42 | 43 |
| 5 | CC5 | 11 | 24 | 32 | 41 |
| 6 | CC6 | 10 | 19 | 22 | 29 |
| 7 | CC7 | 9 | 5 | 12 | 33 |
| 8 | CC8 | 6 | 13 | 15 | 27 |
| 9 | CC9 | 10 | 23 | 27 | 44 |
| 10 | CC10 | 1 | 1 | 9 | 8 |
| 11 | CC11 | 0 | 11 | 16 | 8 |
| 12 | CC12 | 3 | 10 | 15 | 40 |
| 13 | CC13 | 18 | 52 | 52 | 65 |
| 14 | CC14 | 7 | 8 | 8 | 13 |
| 15 | CC15 | 15 | 30 | 30 | 66 |
| 16 | CC16 | 5 | 14 | 14 | 18 |
| 17 | CC17 | — | — | 62 | 70 |

All values are average of triplicate analyses with and SD. of .±.0.2

TABLE 7

Effect of Additional Carbon Sources on the Efficiency of Consortium CC17

| | | % Removal of color | | |
|---|---|---|---|---|
| S. No. | Sample | 24 hrs | 48 hrs | 72 hrs |
| 1 | Effluent + Consortia | 49 | 63 | 72 |
| 2 | Effluent + Consortia + 0.5% Glucose | 60 | 68 | 73 |
| 3 | Effluent + Consortia + 0.75% Glucose | 62 | 69 | 71 |
| 4 | Effluent + Consortia + 1.0% Glucose | 68 | 75 | 79 |
| 5 | Effluent + Consortia + 0.5% Sucrose | 60 | 65 | 73 |
| 6 | Effluent + Consortia + 0.75% Sucrose | 64 | 73 | 75 |
| 7 | Effluent + Consortia + 1.0% Sucrose | 63 | 74 | 75 |

All values are a average of duplicate analyses with an S.D. of .±.0.2

TABLE 8

Effect of Increasing Biomass Levels of Bacteria Individually as well as in the Form of Consortia on Color and Total Lignin Levels of Pulp Mill Effluent

| | % Reduction in color | | % Reduction in Total Lignin | |
|---|---|---|---|---|
| Sample | 24 hrs | 48 hrs | 24 hrs | 48 hrs |
| Effluent + CC17 | 50 | 58 | 16 | 19 |
| Effluent + MTCC 5099 | — | 60 | 18 | 25 |
| Effluent + Bacterium 19 | 48 | 49 | 19 | 29 |
| Effluent + Bacterium 35 | 43 | 48 | 26 | 31 |

All values are an average of three readings with an S.D. of .±.0.5

TABLE 9

Viability of MTCC 5099 in the Effluent during the color reduction experiment in terms of Colony Forming Units (CFU/ml)

| CFU/ml (0 hour) | CFU/ml (24 hour) | CFU/ml (48 hour) |
|---|---|---|
| $9.7 \times 10^9$ | $8.0 \times 10^9$ | $6.1 \times 10^{10}$ |

TABLE 10

Characteristics of Deposit Accession no. MTCC 5099. Analysis of the bacterial strains 7 and 8 was carried out at Deutsche Sammlung von Mikroorganismen und Zellkulturen GmbH (DSMZ), ID No. DSM 03-504/505.
Name of the strain *Pseudomonas aeruginosa*

| Properties of the strain | |
|---|---|
| Shape of cells | Rods |
| Width μm | 0.5-0.7 |
| Length μm | 1.8-3.0 |
| Motility | + |
| Flagella | Polar 1 |
| Gram reaction | − |
| Lysis by 3% KOH | + |
| Aminopeptidase (Cerny) | + |
| Oxidase | + |
| Catalase | + |
| ADH | + |
| Nitrate reduction | + |
| Denitrification | + |
| Urease | + |
| Hydrolysis of gelatin | + |

TABLE 10-continued

Characteristics of Deposit Accession no. MTCC 5099. Analysis of the bacterial strains 7 and 8 was carried out at Deutsche Sammlung von Mikroorganismen und Zellkulturen GmbH (DSMZ), ID No. DSM 03-504/505. Name of the strain *Pseudomonas aeruginosa*

| Utilization of | |
|---|---|
| glucose | + |
| arabinose | − |
| adipate | + |
| malate | + |
| mannitol | + |
| phenylacetate | − |
| citrate | + |
| caprate | + |
| gluconate | + |
| maltose | − |
| n-acetylglucosamine | + |
| azelate | + |
| acetamide | + |
| geraniol | + |
| trehalose | − |
| sorbitol | − |
| citraconate | + |
| Growth at 41° C. | + |
| Levan from sucrose | − |
| Fluorescent pigment | + |
| Pyocyanin | + |

The profile of cellular fatty acids further confirms that the strain is indeed *Pseudomonas aeruginosa*

As shown in Table 10, the bacterial strains identified as strains 7 and 8 were submitted and were identified to be *Pseudomonas aeruginosa* based on an analysis of the morphology and biochemical characteristics of the bacteria. For example, visualization of the bacteria at a magnification of 2700× showed Gram negative rods whose lengths are in the range from about 1.8 µm to about 3.0 µm and whose widths are in the range from about 0.5 µm to about 0.7 µm. The rods were found to be motile due to the presence of a flagella. See FIGS. 1A and 1B. When grown on nutrient agar, eye-shaped colonies having a smooth outer margin are observed. The colonies are fluorescent green in color due to the fluorescent pigment Pyocyanin. Furthermore, biochemical analysis showed that both strains of bacteria are capable of reducing nitrate, in addition to their ability as denitrifying bacteria. It is observed that the bacterial strains 7 and 8 do not require any additional nutrients to be added to the growth medium for survival. Cellular fatty acid profiles for strains 7 and 8 are typical for bacteria that belong to *Pseudomonas aeruginosa*.

Further confirmation is provided by partial sequencing of the 16SrDNA of strain DSM 03-504, which shows a 99.3% similarity to the type strain of this species. Additionally, the comparison of strains 7 and 8 by Riboprintanalysis shows that the two strains belong to the same Ribogroup and should be related. Furthermore, the entire content of the data analysis certificate submitted during the prosecution of the parent application U.S. patent application Ser. No. 11/077,217, filed Mar. 11, 2005, are incorporated fully herein by reference.

Advantages

1. The isolated bacterium is capable of reducing the color of the pulp mill effluent in a reproducible manner.

2. The isolated bacterium remains viable even after the completion of the experiment suggesting its reusability in next set of experiment.

3. The naturally isolated bacterium is non pathogenic and can be cultured on simple nutrient media without any economic burden.

4. This kind of bacterial reduction of color from pulp mill effluents is novel.

What is claimed is:

1. A biologically pure culture of bacterial strain *Pseudomonas aeruginosa*, DSMZ 03-505, having Accession No. MTCC 5099, wherein the strain reduces the color of a waste water effluent in the range from about 50% to 70%.

2. The strain of *Pseudomonas aeruginosa*, DSMZ 03-505, as claimed in claim 1, wherein the strain is gram negative.

3. The strain of *Pseudomonas aeruginosa*, DSMZ 03-505, as claimed in claim 1, wherein the strain is a short rod.

4. The strain of *Pseudomonas aeruginosa*, DSMZ 03-505, as claimed in claim 1, wherein the strain forms eye-shaped colonies when plated on Nutrient agar.

5. The strain of *Pseudomonas aeruginosa*, DSMZ 03-505, as claimed in claim 1, wherein the strain reduces the color of a waste effluent by 70% within 24 hours.

* * * * *